United States Patent
Branovacki

(10) Patent No.: US 8,066,775 B2
(45) Date of Patent: Nov. 29, 2011

(54) JOINT IMPLANT

(76) Inventor: George Branovacki, Chicago, IL (US)

( * ) Notice: Subject to any disclaimer, the term of this patent is extended or adjusted under 35 U.S.C. 154(b) by 89 days.

(21) Appl. No.: 12/483,746

(22) Filed: Jun. 12, 2009

(65) Prior Publication Data

US 2010/0318191 A1    Dec. 16, 2010

(51) Int. Cl.
*A61F 2/30*    (2006.01)

(52) U.S. Cl. .............. 623/18.11; 623/16.11; 623/23.15

(58) Field of Classification Search ............. 623/18.11, 623/22.11–23.44; *A61F 2/30*
See application file for complete search history.

(56) References Cited

U.S. PATENT DOCUMENTS

| | | |
|---|---|---|
| 2,719,522 A | 10/1955 | Hudack |
| 4,163,292 A | 8/1979 | Averett, Jr. |
| 4,422,187 A | 12/1983 | Zweymiiler |
| 4,813,962 A | 3/1989 | Deckner et al. |
| 5,002,581 A | 3/1991 | Paxson et al. |
| 5,201,882 A | 4/1993 | Paxson |
| 5,456,717 A | 10/1995 | Zweymüller et al. |
| 5,472,444 A | 12/1995 | Huebner et al. |
| 5,549,704 A | 8/1996 | Sutter |
| 5,653,764 A | 8/1997 | Murphy |
| 6,306,174 B1 | 10/2001 | Gie et al. |
| 6,676,705 B1 | 1/2004 | Wolf |
| 7,410,488 B2 * | 8/2008 | Janna et al. ............ 606/62 |
| 2006/0058887 A1 * | 3/2006 | DeSmet et al. .......... 623/22.36 |
| 2008/0039950 A1 | 2/2008 | Splieth et al. |
| 2008/0183298 A1 | 7/2008 | McTighe et al. |

* cited by examiner

*Primary Examiner* — Thomas J Sweet
*Assistant Examiner* — Jason-Dennis Stewart
(74) *Attorney, Agent, or Firm* — Greer, Burns & Crain, Ltd.

(57) ABSTRACT

A joint implant, includes a neck and a blade extending along a longitudinal axis and connected to the neck to form a blade plane. A plurality of bores is located in the blade, each of the bores having a central axis, the axes being oriented so that none project at the same angle relative to the blade plane.

13 Claims, 2 Drawing Sheets

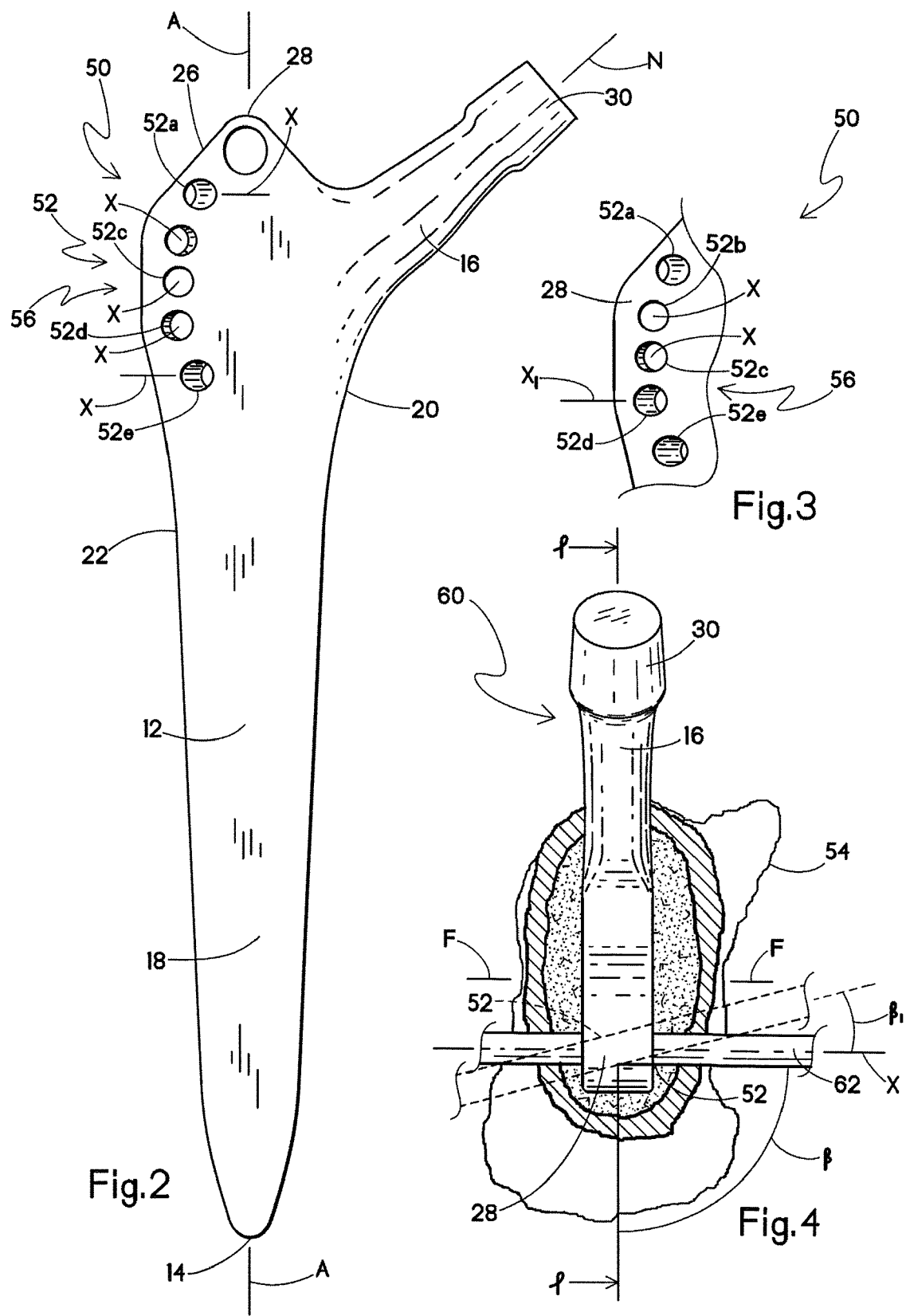

JOINT IMPLANT

BACKGROUND

The present invention relates to joint prostheses, and more specifically to a hip joint prosthesis configured for being anchored in a femur, however other joint implants are contemplated as being suitable with the present invention.

Hip prostheses, also referred to as hip joint implants, are known having a blade-like shaft or stem which is anchored in a patient's femur. A ball is fitted to an upper end of the shaft and is disposed at an angle relative to a longitudinal axis of the shaft to simulate the upper end of the natural femur. In some cases, the shaft is anchored in the femur in a cement-free manner by jamming and/or wedging the shaft into the cortex of a surgically prepared femur. This jamming takes place primarily in the area of the diaphysis, that is, in the distal part of the shaft and requires that the surgically hollowed space and the shaft form and size be carefully matched and adjusted relative to each other. Alternately, some shafts are held in the femur with cement.

During initial installation of the hip implant, it is important to properly align the implant relative to the femur, so that the ball end does not easily become disengaged during the patient's normal range of motion. An artificial hip joint can dislocate if the ball disengages from the socket. There is greater risk just after surgery, before the tissues have healed around the new joint. A hip that dislocates more than once may have to be revised to make it more stable. This requires supplemental surgery.

In some cases, it may also be necessary to remove and re-insert the shaft several times during a surgical procedure. For this reason, the shafts have been provided with a bore in the roof-ridge shaped proximal end which is perpendicular to the sides of the blade to permit the use of a hook-shaped instrument for pulling or driving out the shaft from the femur.

Often, conventional hip joint implants wear out and require surgical intervention to make repairs or to replace worn components. To facilitate the presurgical ordering of spare components, conventional hip joint implants are often provided with a plurality of holes or bores in a manufacturer or designer-specific pattern, so that the particular brand of implant can be recognized on X-rays. The holes are specifically designed to facilitate identification of the implant under X-ray. In many cases, the number, alignment and relative positioning of adjacent bores on the blade are indicative of a particular implant manufacturer.

Regardless of the reason, the removal of an existing hip implant stem is a laborious process, since the patient's bone has usually grown around, and has become integral with the implant. Due to the problems and stress on the patient when an implant is removed, surgeons typically take great pains to obtain a correct initial alignment of the implant relative to the femur to reduce dislocations and subsequent adjustments or removal.

Thus, there is a need for a system to more accurately align hip implants in the femur.

SUMMARY

The above-identified need is met by providing a joint implant with an internal alignment indicator. More specifically, the implant is provided with a plurality of identifier bores in a spaced linear array. A central axis of each bore is incrementally adjusted relative to the adjacent bores, so that when a practitioner sees that a pre-designated bore is visible as totally open, the implant is properly aligned in the femur.

More specifically, a joint implant is provided, including a neck and a blade extending along a longitudinal axis and connected to the neck along a blade plane. A plurality of bores is located in the blade, each of the bores having a central axis, the bore axes being oriented so that none project at the same angle relative to the blade plane.

In another embodiment, a joint implant includes a neck and a blade extending along a longitudinal axis and connected to the neck along a boundary plane. The blade has a pair of opposite wide sides parallel to the plane. A plurality of bores is located in the blade, each of the bores having a central axis. The central bore axes are oriented so that none project at the same angle relative to the plane.

BRIEF DESCRIPTION OF THE DRAWINGS

FIG. 2 is a front perspective view of the present joint implant;

FIG. 3 is a fragmentary front perspective view of the present joint implant rotated 15 degrees from the view shown in FIG. 1; and FIG. 4 is a top view of the present implant shown implanted in a femur and provided with angle indicator rods inserted in the identifier bores.

DETAILED DESCRIPTION

Figure 1:
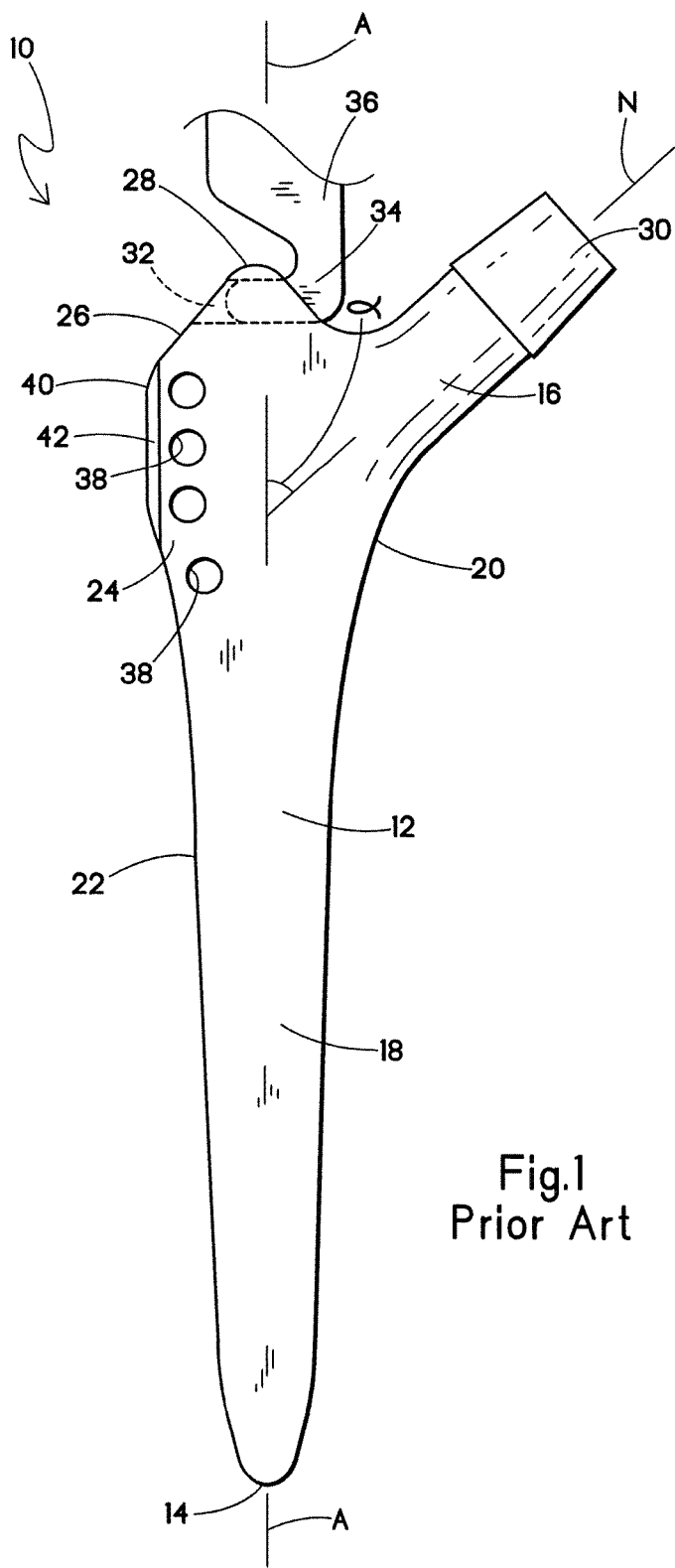
FIG. 1 is a front view of a prior art joint implant.

Referring to FIG. 1, a prior art hip implant or prosthesis the prosthesis is generally indicated at 10 and includes a blade 12 which extends from a distal end or tip 14 along a straight longitudinal axis A. The blade 12 is connected to a neck 16 opposite the tip 14, the neck extending along a blade plane P-P (FIG. 4) which extends laterally relative to the axis A and also to an axis N of the neck 16, which extends at an acute angle $\alpha$ to the axis A. While in the preferred embodiment the blade 12 is generally rectangular or polygonal in lateral cross-section, other blade configurations are contemplated, including circular or oval cross-sections, resulting in a generally cylindrically appearing blade.

More specifically, the depicted blade 12 has a pair of opposite wide sides 18 extending parallel to the blade plane P-P, a medial narrow side 20 which extends from the neck 16 on a continuous curve and a lateral narrow side 22 which extends on a conical taper from the tip 14 to a trochanter wing 24. The wing 24, in turn, extends into a roof-ridge shaped shoulder 26 at a proximal end 28 of the blade 12. As shown, the shoulder 26 is disposed symmetrically along the longitudinal axis A.

In addition, the implant 10 is also provided with a peg 30 on the neck 16 for receiving a spherical joint head (not shown) as is known in the art. Also as known in the art, the specific configuration or construction of the joint head may vary with the model of the implant.

A lifting aperture 32 is provided in the shoulder 26, the aperture extending parallel to the blade plane P-P. In the illustrated embodiment, the lifting aperture 32 intersects and extends perpendicular to the longitudinal axis A; however, other orientations are contemplated. As indicated in FIG. 1, the lifting aperture 32 is dimensioned to receive a hook 34 of a removal instrument 36 (shown schematically). Such a hook instrument 36 serves simultaneously for guiding and aligning the blade 12 while fitting the blade into a surgical opening. An angle of the hook 34 relative to an axis of the instrument 36 may, of course, be adjusted to correspond with the angle of the lifting aperture 32 relative to the longitudinal axis A.

The trochanter wing 24 is provided with perforations or bores 38 which are typically disposed in a sequence or pattern for identifying the implant in a manufacturer-specific manner, such bores 38 being visible on X-rays of a patient having such an implant 10. In some cases, an outer margin 40 of the trochanter wing 24 may have a tapered area 42.

Referring now to FIGS. 2-4, the present implant is generally designated 50 as depicted is similar in construction to the prior art implant 10; however other configurations are contemplated, including but not limited to variations in the shape, cross-section and length of the blade 12, and configurations in the neck 16.

An important feature of the implant 50 is that the bores 38 are replaced by a plurality of bores 52 located in the blade 12, each of the bores having a central axis X. The bores 52 are disposed in the blade 12 so that the axes X are oriented such that none project at the same angle β (FIG. 4) relative to the blade plane P-P. Such an orientation of the bores 52 provides the installing surgeon with a visual indication of the angular orientation of the implant 50 relative to the femur 54 (FIG. 4). While the present bores 52 are located on the trochanter wing 28, it is contemplated that they may be located elsewhere on the implant 50 depending on the application.

More specifically, depending on the orientation of the implant 50 in the femur 54, certain of the bores 52 will be visible to the surgeon as a complete circle. Depending on the type and size of the implant, the particular bore 52a, 52b, 52c, 52d, 52e which is visible as a circle will indicate the angular orientation of the implant, such orientations being determined by the manufacturer. Also, as is the case with prior art implants, the bores 52 provide a source-specific image on X-ray to facilitate identification of the manufacturer of the implant for ordering spare parts prior to surgery. While blind end or closed bores 52 are contemplated, it is preferred that the bores extend through the blade 12 or communicate from one wide side 18 to the other.

Referring now to FIG. 2, by varying the angular orientation of the axes X, the angular orientation of the implant 50 relative to the femur 54 is shown by a visual survey of the shapes of the bores 52 at a given position. In other words, as the implant 50 is rotated about the axis A, the appearance of each bore 52 will change. Some bores, such as bores 52a and 52e at the ends of a bore sequence 56 will be almost completely eclipsed, or be visible as cat-eye shaped ellipses, bores 52b and 52d are only partially obscured, and only central bore 52c is visible as a complete circle.

Thus, comparing FIGS. 2 and 3, wherein FIG. 2 depicts a 0° anteverted orientation and FIG. 3 depicts a 15° anteverted orientation, with progressive angular rotation of the implant 50 about the axis A, the member of bores 52a-e which is visible as a complete circle will vary along the sequence 56. This angular orientation can be specified by the manufacturer to represent a particular angular orientation, such that if the bore 52b is circular, the implant 50 is oriented at 15° relative to a base position, and if the bore 52a is circular, the implant is oriented at 20° relative to a base position, etc. The angular orientation of the particular bores 52a-e may be varied to suit the application, the size of the implant 50 and the particular manufacturer's configuration.

In the preferred embodiment, the bores 52a-e include a central bore 52c being oriented so that its central axis X is normal relative to the plane P-P in a base orientation, and the remaining bores 52a, 52b, 52d and 52e are oriented so that their corresponding axes X are angularly adjusted relative to the axis X of the central bore 52c. More specifically, the bores 52b and 52d located adjacent the central bore 52c are adjusted angularly relative to the axis X of the central bore the same amount but in mirror image relationship to each other. In other words, bore 52b is oriented at +15° relative to the axis of the bore 52c, while the axis of the bore 52d is oriented at −15° relative to the axis of the central bore 52c. The next successive bores 52a and 52e on either side of the central bore 52c are adjusted the same amount but in mirror image relationship to each other. Specifically, the axes of the bores 52a and 52e are adjusted +25° and −25° relative to the central bore axis. The axes X of the bores 52a-e are oriented such that none project at the same angle relative to the plane P-P.

Also, while other orientations are contemplated, in the preferred embodiment, the sequence 56 of the bores 52a-e is linearly disposed on the blade 12 generally parallel to the longitudinal axis A. Also, the orientation of the angular variations of the bores 52a-e relative to each other are preferably in a plane transverse to the longitudinal axis A. However, it is also contemplated that such variations occur in a plane parallel too the axis A. It should also be noted that the aperture 32 is oriented normally in the implant 50 to its position in the implant 10, and either position is considered suitable, depending on the application.

Referring now to FIG. 4, an alternate embodiment of the present implant is generally designated 60. Corresponding elements shared with the implants 10 and 50 are designated with the identical reference numbers. The significant variation of the implant 60 is that indicator rods 62 are inserted into one or more of the bores 52a-e to provide a more visible angular orientation of the implant 60 to the femur 54. In one example, the angular orientation of the indicator rods 62 can be compared to a vertical axis F of the patient's foot, for example as positioned on the operating table. Thus, once the rods 62 are inserted, the implant 60 can be positioned relative to the femur 54 until the rod points in a direction aligned with the axis F.

While a particular embodiment of the present joint implant has been shown and described, it will be appreciated by those skilled in the art that changes and modifications may be made thereto without departing from the invention in its broader aspects and as set forth in the following claims.

What is claimed:

1. A joint implant for attachment to a limb, comprising:
   a neck; and
   a blade extending along a longitudinal axis and connected to said neck to form a blade plane;
   a plurality of bores located in said blade, each of said bores having a central axis; said axes being oriented so that none project at the same angle relative to said blade plane, wherein said bores are configured to provide a visual representation of an angular orientation of said joint implant relative to the limb for facilitating alignment of said implant as it is implanted into the limb.

2. The joint implant of claim 1 wherein said plurality of bores includes a central bore being oriented so that said central axis is normal relative to said plane in a base orientation, the remaining bores in said plurality being oriented so that their corresponding axes are angularly adjusted relative to said central axis of said central bore.

3. The joint implant of claim 1 wherein said plurality of bores are linearly arranged on said blade generally parallel to said longitudinal axis.

4. The joint implant of claim 1 wherein said bores located adjacent a central bore are adjusted angularly relative to said central bore the same amount but in mirror image relationship to each other.

5. The joint implant of claim 4 wherein said angular adjustments vary in a plane transverse to said longitudinal axis.

6. The joint implant of claim 4 wherein successive bores on either side of said central bore are adjusted the same amount but in mirror image relationship to each other.

7. The joint implant of claim 4 wherein there are two bores on each side of said central bore, said bores closest to said central bore being adjusted +15° and −15° relative to said central bore axis.

8. The joint implant of claim 7 wherein two bores next adjacent said closest bores are adjusted +25° and −25° relative to said central bore axis.

9. The joint implant of claim 1 wherein said bores communicate between said sides.

10. The joint implant of claim 1 further including at least one indicator rod releasably inserted into a corresponding one of said bores to provide a more visible indicator of said angular orientation of said implant relative to the limb.

11. The joint implant of claim 1 wherein said blade further includes a medial narrow side extending from said neck on a continuous curve, a lateral narrow side, a roof-ridge shaped shoulder between said lateral narrow side and said neck and a bore extending through said shoulder for reception of a hook of a removal instrument from opposite sides in the direction of said neck.

12. The joint implant of claim 1 wherein said blade further includes a trochanter wing between said shoulder and said lateral narrow side, and said bores are located in said trochanter wing.

13. A joint implant for attachment to a limb, comprising:
a neck; and
a blade extending along a longitudinal axis and connected to said neck along a boundary plane, said blade having a pair of opposite wide sides being parallel to the plane;
a plurality of bores located in said blade, each of said bores having a central axis; said axes being oriented so that none project at the same angle relative to said plan; wherein said bores are configured to provide a visual representation of an angular orientation of said implant relative to the limb for facilitating alignment of said implant as it is implanted into the limb.

* * * * *

UNITED STATES PATENT AND TRADEMARK OFFICE
CERTIFICATE OF CORRECTION

| | | |
|---|---|---|
| PATENT NO. | : 8,066,775 B2 | Page 1 of 1 |
| APPLICATION NO. | : 12/483746 | |
| DATED | : November 29, 2011 | |
| INVENTOR(S) | : George Branovacki | |

It is certified that error appears in the above-identified patent and that said Letters Patent is hereby corrected as shown below:

On the Title Page:

Under "(56) References Cited" please delete "Zweymiiler" and insert the following: --Zweymüller--.

In the Specification:

In Col. 2, Lns. 31-32, delete "the prosthesis".

In Col. 4, Ln. 16, delete "too" and insert --to--.

In the Claims:

In Claim 12, Col. 6, Ln. 1, delete "claim 1" and insert --claim 11--.

Ln. 12, delete "plan;" and insert --plane,--.

Signed and Sealed this
Twenty-sixth Day of August, 2014

Michelle K. Lee
*Deputy Director of the United States Patent and Trademark Office*